(12) United States Patent
Castro

(10) Patent No.: US 12,262,931 B2
(45) Date of Patent: Apr. 1, 2025

(54) SURGICAL FASTENER COMBINATION

(71) Applicant: Blue Sky Technologies, LLC, Louisville, KY (US)

(72) Inventor: Frank Castro, Louisville, KY (US)

(73) Assignee: BLUE SKY TECHNOLOGIES, LLC, Louisville, KY (US)

( * ) Notice: Subject to any disclaimer, the term of this patent is extended or adjusted under 35 U.S.C. 154(b) by 259 days.

(21) Appl. No.: 17/921,680

(22) PCT Filed: Dec. 6, 2021

(86) PCT No.: PCT/US2021/061959
§ 371 (c)(1),
(2) Date: Oct. 27, 2022

(87) PCT Pub. No.: WO2022/132474
PCT Pub. Date: Jun. 23, 2022

(65) Prior Publication Data
US 2023/0165612 A1    Jun. 1, 2023

Related U.S. Application Data

(60) Provisional application No. 63/125,443, filed on Dec. 15, 2020.

(51) Int. Cl.
*A61B 17/84*    (2006.01)
(52) U.S. Cl.
CPC .......... *A61B 17/844* (2013.01); *A61B 17/846* (2013.01)

(58) Field of Classification Search
CPC . A61B 17/844; A61B 17/846; A61B 17/8625; A61B 17/863; A61B 17/8635; A61B 17/864; A61B 17/8685; A61B 2017/8655; F16B 13/0808
USPC ......................................... 411/340, 344–346
See application file for complete search history.

(56) References Cited

U.S. PATENT DOCUMENTS

| | | | |
|---|---|---|---|
| 4,636,121 A * | 1/1987 | Miller | F16B 39/04 411/21 |
| 5,601,559 A | 2/1997 | Melker et al. | |
| 6,277,122 B1 | 8/2001 | McGahn et al. | |
| 6,923,830 B2 | 8/2005 | Michelson | |
| 8,221,479 B2 | 7/2012 | Glazer et al. | |
| 8,449,583 B2 * | 5/2013 | Krebs | A61F 2/3662 606/62 |
| 8,771,359 B2 | 7/2014 | Lee | |
| 9,566,099 B2 | 2/2017 | Wenger et al. | |
| 11,653,952 B2 * | 5/2023 | Ball | A61B 17/686 606/279 |
| 2017/0296344 A1 | 10/2017 | Souza et al. | |
| 2020/0197061 A1 | 6/2020 | Castro | |

* cited by examiner

*Primary Examiner* — Tracy L Kamikawa
(74) *Attorney, Agent, or Firm* — BUSINESS PATENT LAW, PLLC

(57) ABSTRACT

A surgical fastener combination for use in posterior surgeries requiring require fusion between the occiput and pelvis. Among other things, the surgical fastener combination includes first and second cutters.

5 Claims, 4 Drawing Sheets

SURGICAL FASTENER COMBINATION

PRIORITY

Applicant claims the benefit of U.S. Provisional Application No. 63/125,443—Surgical Fastener Combination—filed on Dec. 15, 2020.

BACKGROUND OF THE INVENTION

A. Field of the Invention

The present invention is surgical fastener combination provided with first and second components. First and second components include first and second cutters. In select preferred embodiments, the surgical fastener combination is provided with a head that can be fixed or polyaxial. Except for the head, the surgical fastener is threadless.

B. Description of the Previous Art

Any discussion of references cited in this Description of the Previous Art merely summarizes the disclosures of the cited references and Applicant makes no admission that any cited reference or portion thereof is relevant prior art. Applicant reserves the right to challenge the accuracy, relevancy and veracity of the cited references.

References that may indicate a state-of-the-art for the current invention include: 1) U.S. Pat. No. 6,277,122-McGahan et al. discloses a distraction instrument with fins for maintaining insertion location; 2) U.S. Pat. No. 6,923,830-Michelson discloses a spinal fusion implant having deployable bone engaging projections; and 3) U.S. Pat. No. 8,771,359-Lee discloses a spinal implant device.

Among other things, none of the above listed references disclose a surgical fastener combination adapted for implantation into a joint space or a surgically created cavity; the surgical fastener combination comprising: a) an inward side of a first cutter attached to an outer side of a cylindrical shell; the inward side parallel a longitudinal axis (X-X) of the surgical fastener combination, wherein relative to the longitudinal axis (X-X) and the anterior portion of the first anterior edge, the first anterior edge is sloped at an angle of about 30 degrees to about 155 degrees; b) an inward side of a second cutter attached to an outward side of a shaft; the inward side parallel the longitudinal axis of the surgical fastener combination, wherein a portion of the shaft 210 rides in a hollow of the cylindrical shell, and relative to the longitudinal axis (X-X) and the anterior portion of the second anterior edge, the second anterior edge is sloped at an angle of about 30 degrees to about 155 degrees; and c) a head connected to the surgeon facing end of the shaft and adapted to receive an apparatus distinct from the surgical fastener combination.

SUMMARY OF THE INVENTION

Successful fusion of a joint or broken bone is directly correlated to the construct rigidity surrounding the area of interest. Current spinal instrumentation relies on screws being anchored into bone and rods connecting to these anchors. Loosening of current constructs occurs primarily at the bone-anchor interface. Toggling of the screws can allow for enlargement of the insertion pathway. As the diameter of the insertion pathway increases, there is greater risk of the screw backing out and construct failure. The current invention can be utilized for arthrodesis procedures of the cervical, thoracic and lumbar spine, as well as the sacroiliac joint or other similar joints.

The biomechanical strength of traditional threaded fixation screws is dependent upon several design characteristics. Larger diameter screws are stronger and more difficult to extract due to increased surface area (friction). The thread pitch, or difference between the inner diameter and the outer diameter, also influences resistance to pull out or back out. The larger the pitch, the greater the resistance to pull out. Biomechanical studies have demonstrated that the volume of bone between screw threads can influence the screw's resistance to pull out. Those skilled in the art recognize that the type and quality of bone are important variables influencing resistance to pull out. Patients with osteoporotic bone have significantly less dense bone than patients with normal bone densities. The contribution of the cancellous bone between the screw threads in patients with osteoporosis is less than patients of normal bone density. In some osteoporotic patients, the screw's fixation strength and resistance to pull out can be determined by the volume of cortical bone in one or two threads of a traditional fixation screw.

Long surgical constructs, such as those used for scoliosis or deformity correction surgery, are often anchored into the sacrum or ilium. These constructs are usually anchored with a large diameter threaded screw. The biophysical forces transmitted to these implanted screws can lead to loosening, construct failure, pain and additional revision surgery.

Many of traditional surgical screws include thread lengths of one to two millimeters that determine the screw's fixation strength. The current surgical fastener provides a potential fixation surface area of from about three to about ten times more than traditional fixation screws. In use, the potential surface area of the surgical fastener is generally juxtaposed the cortical bone—the patient's strongest bone. Cutters of the current invention can be provided with surface treatments and apertures that can encourage bone ingrowth, long-term construct stability and arthrodesis.

When rotated, the surgical fastener combination can be adapted to cut cartilage, cortical bone or other tissues that can provide exposure of bone to another bony surface. Exposing two bony surfaces can increase the probability the bony surfaces of the surfaces uniting into a solid fusion. The current invention may facilitate reapproximation of two joint surfaces that have experienced a distractive deformity from trauma or tumor. Prior to cutting through the first articular surface, the cutters can guide the bone back towards its anatomic position. Once the cutters cross both articular surfaces, forward pressure on the cutters compresses the two surfaces and the cutters can prevent retropulsion. When the invention's cutters are placed across a joint, it may also facilitate fusion by exposing a conduit for bone to form across the joint. When the cutters are positioned completely across a joint, it may compress the articular or bony surfaces. Such imposed motion limitation may result in joint ankylosis.

Among other things, the surgical fastener combination's head can: limit the depth the combination can be inserted through the incision into the surgically created cavity or joint space; be connected with other surgical apparatus, such as, rods, plates or other fixation devices; and allow application of increased torque to the surgical fastener combination.

Intentional or unintentional rotation of threaded devices can lead to displacement of the device into or towards an undesirable location resulting in damage or dysfunction to either a nerve or blood vessel. Those skilled in the art recognize that expulsion of a surgical screw results in an unstable screw that can increase the risk of non-fusion or spinal deformity. Among other things, the surgical fastener combination can be provided with a head of sufficient area to prevent over-insertion into the surgically created cavity or joint space. Depending on medical and/or surgical parameters, the current invention can be adapted to either compress or distract a joint. By way of illustration, when distraction of the posterior cervical facet joint occurs, the adjacent neuroforamin is enlarged and indirect decompression of the exiting nerve root can occur. According to the current state-of-the art, threaded surgical screws cannot provide this benefit.

Subsequent to insertion into a surgically created cavity or joint space with adequate outward tissue remaining proximate the insertion point, rotating the surgical fastener combination from about from about 30 degrees to about 150 degrees can improve resistance to pull out forces.

An aspect of the present invention is to provide a surgical fastener combination.

Still another aspect of the present invention is to provide a surgical fastener combination with an anterior tip and a head opposite the anterior tip.

It is yet another aspect of the present invention to provide a surgical fastener combination with either a fixed head or a polyaxial head.

Still another aspect of the present invention is to provide a surgical fastener combination with a receptacle adapted to receive an apparatus distinct from the surgical fastener.

It is still another aspect of the present invention to provide a surgical fastener combination with two cutters to cut the biological structure or tissue.

Yet still another aspect of the present invention is to provide a surgical fastener combination including a second component carried by a first component.

Still another aspect of the present invention is to provide a surgical fastener combination where the attachment or posterior angles of the cutters can vary with predetermined surgical parameters.

It is still another aspect of the present invention to provide a surgical fastener combination where only the head is provided with threads.

A preferred embodiment of the current invention can be described as a surgical fastener combination adapted for implantation into a joint space or a surgically created cavity; the surgical fastener combination comprising: a) a first component comprising: i) a sloped anterior tip connected to a cylindrical shell including a surgeon facing end; ii) the cylindrical shell comprising: a hollow extending from about the sloped anterior tip to the surgeon facing end; a slot extending lengthwise from the surgeon facing end to about the midpoint of the first component; and a catch extending through the cylindrical shell and communicating with the slot, wherein the catch is of lesser length than the slot; and iii) a first cutter, extending away from a longitudinal axis (X-X) of the surgical fastener combination, connected to an outer side of the cylindrical shell; the first cutter comprising: a first anterior edge adapted to cut tissue in a first direction; a first face and a second face adapted to disrupt adipose, muscle, bone, joint capsule tissues, cartilage and/or bone when the first cutter is rotated relative to the longitudinal axis (X-X); and a dull first posterior end; b) a second component comprising: i) a shaft (210) comprising an anterior end and a surgeon facing end, wherein the anterior end is configured to ride in the hollow and engage an inner wall of the cylindrical shell proximate the first component's anterior tip; and ii) a second cutter, extending away from the longitudinal axis (X-X) of the surgical fastener combination, connected to an outward side of the shaft and configured to fit within the catch; the second cutter comprising: a second anterior edge adapted to cut tissue in the first direction; a third face and a fourth face adapted to disrupt adipose, muscle, bone, joint capsule tissues, cartilage and/or bone when the second cutter is rotated relative to the longitudinal axis (X-X); and a dull second posterior end; and c) a head connected to the surgeon facing end of the second component and adapted to receive an apparatus distinct from the surgical fastener combination.

Another preferred embodiment of the current invention can be described as a surgical fastener combination adapted for implantation into a joint space or a surgically created cavity; the surgical fastener combination comprising: a) a first component comprising: i) an exterior cylindrical shell including an inward hollow adapted to receive a second component, wherein the second component rides in the inward hollow; ii) a first cutter, extending away from a longitudinal axis (X-X) of the surgical fastener combination, connected to an outer side of the cylindrical shell; the first cutter comprising a first anterior edge adapted to cut tissue in a first direction; iii) a catch extending through the cylindrical shell adapted to receive a portion of the second component; b) the second component comprising: i) a shaft including a second cutter, extending away from a longitudinal axis (X-X) of the surgical fastener combination, attached to an outward side of the shaft; and ii) the second cutter comprising a second anterior edge adapted to cut tissue in the first direction, wherein a portion of the second cutter is adapted to be held in the catch; and c) a head connected to the surgeon facing end of the second component and adapted to receive an apparatus distinct from the surgical fastener combination.

Still another preferred embodiment of the current invention can be described as a surgical fastener combination adapted for implantation into a joint space or a surgically created cavity; the surgical fastener combination comprising: a) an inward side of a first cutter attached to an outer side of a cylindrical shell; the inward side parallel a longitudinal axis (X-X) of the surgical fastener combination, wherein relative to the longitudinal axis (X-X) and the anterior portion of the first anterior edge, the first anterior edge is sloped at an angle of about 30 degrees to about 155 degrees; b) an inward side of a second cutter attached to an outward side of a shaft; the inward side parallel the longitudinal axis of the surgical fastener combination, wherein a portion of the shaft 210 rides in a hollow of the cylindrical shell, and relative to the longitudinal axis (X-X) and the anterior portion of the second anterior edge, the second anterior edge is sloped at an angle of about 30 degrees to about 155 degrees; and c) a head connected to the surgeon facing end of the shaft and adapted to receive an apparatus distinct from the surgical fastener combination.

It is the novel and unique interaction of these simple elements which creates the spinal implant combination within the ambit of the present invention. Pursuant to the Articles of the Patent Cooperation Treaty and/or Title 35 of the United States Code, select preferred embodiments of the current invention follow. However, it is to be understood that the descriptions of the preferred embodiments do not limit the scope of the present invention.

DESCRIPTION OF THE PREFERRED EMBODIMENTS

Figure 1:
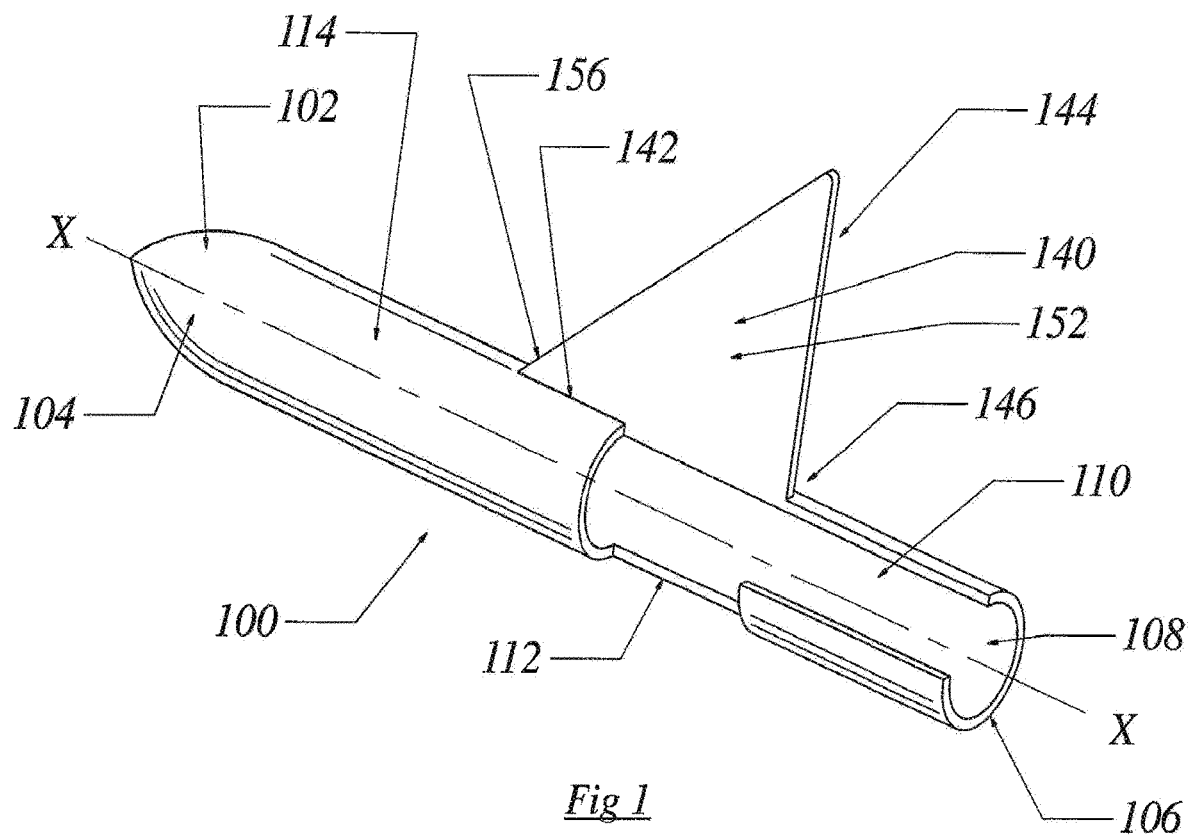
FIG. 1 is a perspective of a preferred embodiment of a first component of the surgical fastener combination.

Although the disclosure hereof is detailed to enable those skilled in the art to practice the invention, the embodiments published herein merely exemplify the present invention.

As used herein, with respect to the surgical fastener combination (60): 1) "anterior" of the surgical fastener combination (60) means the side of the surgical fastener combination (60) most distant from the surgeon and 2) "posterior or surgeon-facing end" of the surgical fastener combination (60) means the side of the surgical fastener combination (60) nearest the surgeon.

In the most general sense, the present invention can result in joint arthrodesis where the surgical fastener combination is surgically inserted into or across a joint space or surgically created cavity. Depending on surgical parameters, one or more surgical fastener combinations can be associated with the same surgically created cavity or joint space. The current surgical fastener combination can be useful for surgeries that can assist in stabilizing injured, deformed and or degenerative joints. Preferred embodiments of the current invention can be employed with ankle, cervical, hand, skull, sacroiliac or other orthopaedic procedures. It appears that the present system is particularly useful for posterior fusions from the occipital region to the pelvis, including the sacroiliac joints. However, the current invention can also be used to fuse the tibia to the talus, the talus to the calcaneus, and metacarpals to the phalanges.

Preferred embodiments of the current surgical fastener combinations can be manufactured of titanium alloys, stainless steel, non-resorbable polymers or any other composition acceptable in the art. Meeting a long felt but unfilled need in the orthopaedic surgical arts, the novel and unique structures of the present surgical fastener combinations allow the surgical team to, among other things, simplify previous procedures.

With reference to FIGS. 1-4, the present invention has a first component (100) and a second component (200). In use, both components (100, 200) share the longitudinal axis of the surgical fastener combination (60).

Among other things, the first component (100) includes a generally blunt anterior tip (102), a cylindrical shell (104) and a first cutter (140). First cutter (140) is rotatable and capable of dissecting through adipose, muscle, bone, joint capsule tissues, cartilage and/or bone. First cutter (140) can be associated with the creation of the surgical cavity and can morselize bone in preparation for fusion.

Among other things, the second component (200) includes shaft (210) configured to engage the inner side (116) of the cylindrical shell (104) of first component (100). Shaft (210) is provided with second cutter (240). Second cutter (240) is rotatable and capable of dissecting through adipose, muscle, bone, joint capsule tissues, cartilage and/or bone. Second cutter (240) can also be associated with the creation of the surgical cavity and can morselize bone in preparation for fusion.

The novel and unique structures of the current surgical fastener combination (60) meet long felt but unfilled needs in the orthopedic surgical arts of allowing implantation of the current surgical fastener combination through the smallest possible surgical incision while providing resistance to pull out that can exceed currently available surgical fasteners.

In select preferred embodiments, head (270) can be connected to the surgeon facing end of shaft (210) of second component (200). Head (270) can be provided with receptacle (272) and lateral openings (274) adapted to receive an apparatus distinct from the surgical fastener combination (60). Depending on surgical requirements, head (270) can be either a fixed or polyaxial head (270). Some preferred embodiments include an extender (280) connecting head (270) to shaft (210). Utilization of extender (280) allows polyaxial head (270) movement in a multitude of directions relative to the longitudinal axis of surgical fastener combination (60).

Figure 2:
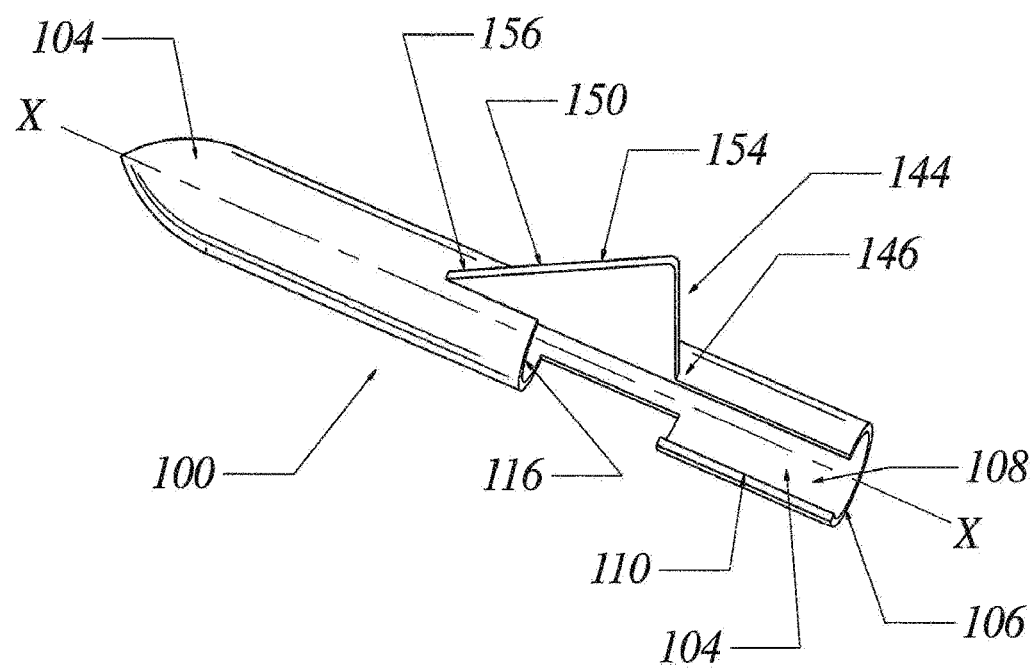
FIG. 2 is a second perspective of the FIG. 1 preferred embodiment of surgical fastener combination where the surgical fastener (100) was rotated approximately twenty degrees.

FIGS. 1 and 2 are perspectives of first component (100) of surgical fastener combination (60). First component (100) is provided with sloped anterior tip (102) connected to cylindrical shell (104). Cylindrical shell (104) includes surgeon facing end (106), hollow (108), slot (110) and catch (112). Sloped anterior tip (102) is generally blunt. Hollow (108) extends from about the sloped anterior tip (102) to surgeon facing end (106) of cylindrical shell (104). A catch (112) of lesser length than slot (110) extends through cylindrical shell (104) and communicates with slot (110).

Inward side (142) of first cutter (140) is attached to the outer side (114) of cylindrical shell (104). Inward side (142) is parallel the longitudinal axis of surgical fastener combination (60). The first attachment or first posterior angle (146) of the first posterior end (144) of first cutter (140) is from about 30 degrees to about 155 degrees relative to the outer side (114) of the cylindrical shell (104). First posterior end (144) of first cutter (140) is dull. In select preferred embodiments of first cutter (140), relative to the longitudinal axis (X-X) and anterior portion (156) of the first anterior edge (150), first anterior edge (150) is sloped at an angle of about 30 degrees to about 155 degrees.

When cylindrical shell (104) is rotated, first cutter (140) is also rotated. First cutter (140) is provided with a first sharp edge (150) adapted to cut tissue as first cutter (140) is advanced into the joint space or surgically created cavity. First cutter (140) is also provided with first side (152) and second side (154). On rotation of cylindrical shell (104), first face (152) and second face (154) of first cutter (140) are adapted to disrupt adipose, muscle, bone, joint capsule tissues, cartilage and/or bone so that surgical fastener combination (60) can be fitted into the joint space or the surgically created cavity.

Figure 3:
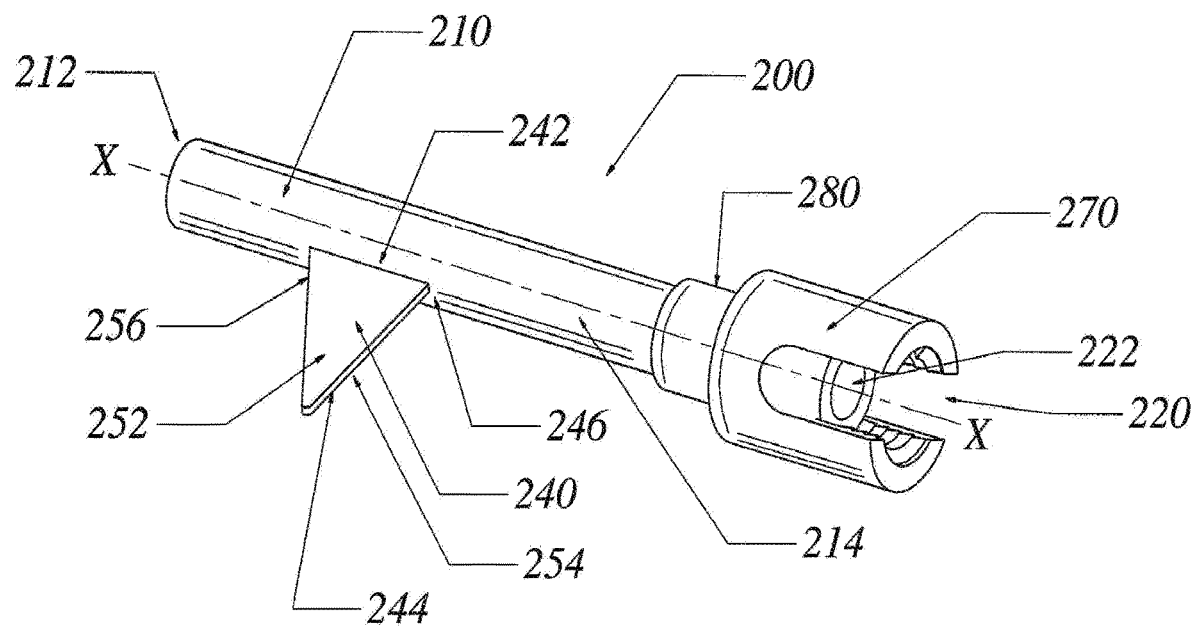
FIG. 3 is a perspective of a preferred embodiment of a second component of the surgical fastener combination.
Figure 4:
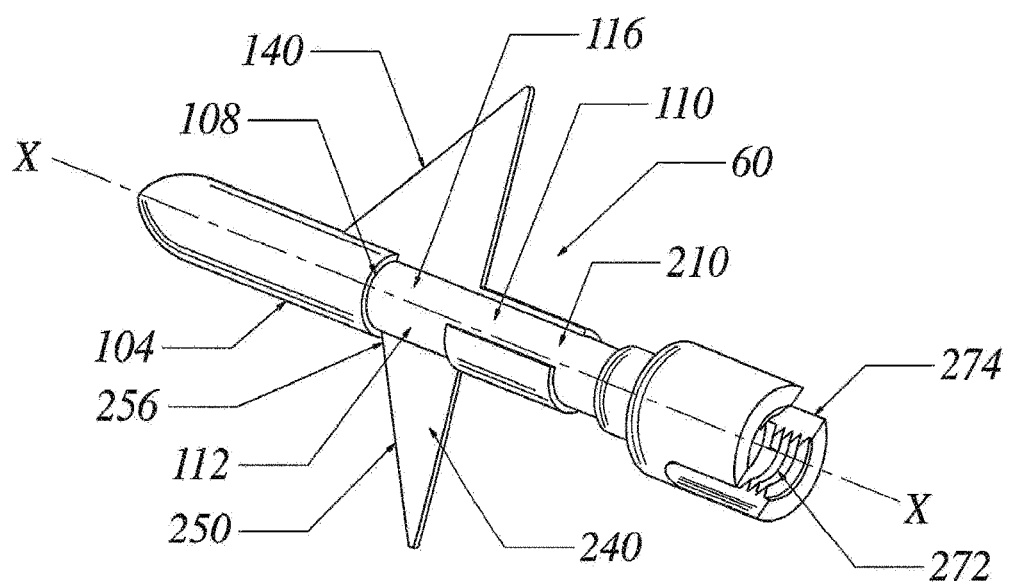
FIG. 4 is a perspective of assembled first and second components of the surgical fastener combination.

With reference to FIG. 3, second component (200) is provided with shaft (210), second cutter (240) and head (270). Shaft (210) includes anterior end (212) outward side (214) and surgeon facing end (220). Within the scope of the current invention, select preferred embodiments of shaft (210) are composed of a solid interior mass or a generally solid interior mass with an inner channel (222) extending from the anterior end (212) through the surgeon facing end (220).

Inward side (242) of second cutter (240) is attached to the outward side (214) of shaft (210). Inward side (242) is parallel the longitudinal axis of surgical fastener combination (60). The second attachment or first posterior angle (246) of the second posterior end (244) of second cutter (240) is from about 30 degrees to about 155 degrees relative to the outward side (214) of shaft (210). Second posterior end (244) of second cutter (240) is dull. In select preferred embodiments of second cutter (240), relative to the longitudinal axis (X-X) and anterior portion (256) of the second anterior edge (250), the second anterior edge (250) is sloped at an angle of about 30 degrees to about 155 degrees.

When shaft (210) is rotated, second cutter (240) is also rotated. Second cutter (240) is provided with a second sharp edge (250) adapted to cut tissue as second cutter (240) is advanced into the joint space or surgically created cavity. Second cutter (240) is also provided with third face (252) and fourth face (254). On rotation of surgical fastener combination (60), third face (252) and fourth face (254) of second cutter (240) are adapted to disrupt adipose, muscle, bone, joint capsule tissues, cartilage and/or bone so that surgical fastener combination (60) can be fitted into the joint space or the surgically created cavity.

As shown in FIG. 3, head (270) is attached to surgeon facing end (220) of shaft (210). As shown, polyaxial head (270) of surgical fastener combination (60) is adapted for connection with a device (not shown) distinct from surgical fastener combination (60). Examples of devices connectable to head (270) include but are not limited to: rods, bars, cross-links, screws and locking nuts.

In operation of the current surgical fastener combination (60), shaft (210) is received by hollow (108), slot (110) and inner side or wall (116) of cylindrical shell (104). Riding through slot (110), second cutter (240) of shaft (210) can be positioned proximate catch (112) of cylindrical shell (104). Catch (112) of cylindrical shell (104) is sized to receive a portion of second cutter (240) proximate inward side (242) of second cutter (240). Third and fourth faces (252, 254), posterior end (244) and second sharp edge (250) of second cutter (240) extend outward from shaft (210) and through catch (112) of cylindrical shell (104) Securing second cutter (240) in catch (112) may be accomplished by rotating first cutter (140) clockwise or second cutter (240) counterclockwise. When second cutter (240) is secured in catch (112), clockwise rotation of shaft (210) rotates first cutter (140) and second cutter (240) in the same direction. Counterclockwise rotation of first cutter (140) will decrease the angular distance between first cutter (140) and second cutter (240).

Figure 5:
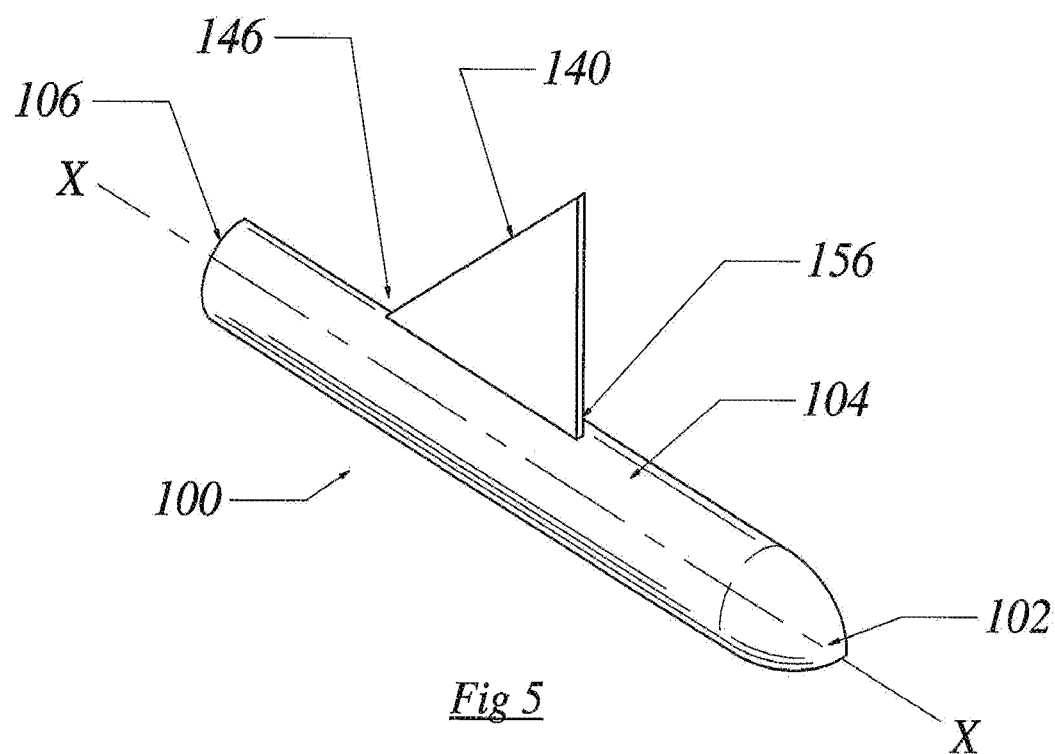
FIGS. 5-7 are perspectives showing additional angles of attachment of first cutter to cylindrical shell of first component of the surgical fastener combination.
Figure 6:
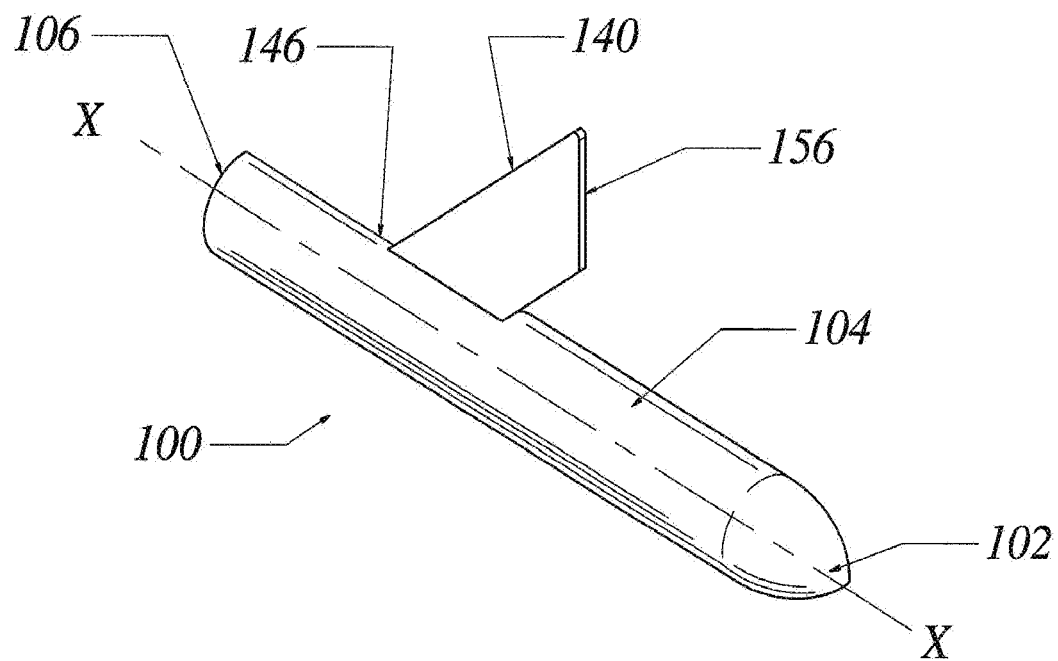
Figure 7:
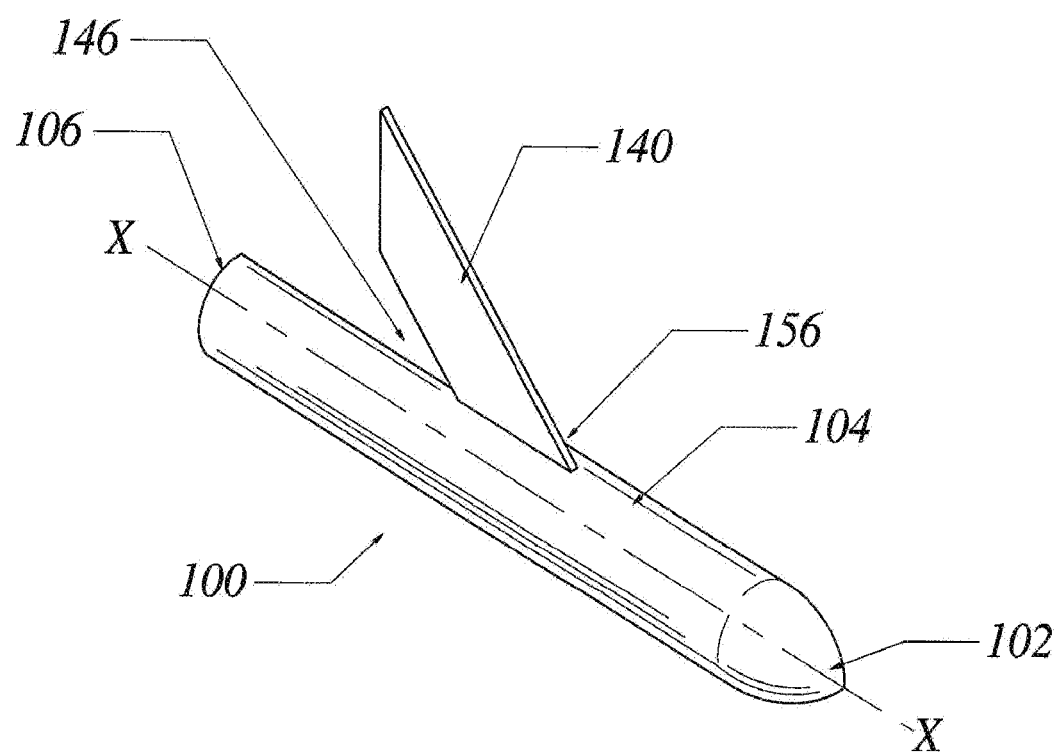

FIGS. 5-7 exemplify embodiments of first component (100) utilizing different attachment angles (146) for first cutter (140) than attachment angles (146) previously disclosed in FIGS. 1-4.

Select preferred embodiments of the current invention have been disclosed and enabled as required by Title 35 of the United States Code and/or the Articles of the Patent Cooperation Treaty.

What is claimed is:

1. A surgical fastener combination (60) adapted for implantation into a joint space or a surgically created cavity; the surgical fastener combination (60) comprising:
   a) a first component (100) comprising:
      i) a sloped anterior tip (102) connected to a cylindrical shell (104) including a surgeon facing end (106);
      ii) the cylindrical shell (104) comprising:
         a hollow (108) extending from about the sloped anterior tip (102) to the surgeon facing end (106);
         a slot (110) extending lengthwise from the surgeon facing end (106) to about a midpoint of the first component (100); and
         a catch (112) extending through the cylindrical shell (104) and communicating with the slot (110), wherein the catch (112) is of lesser length than the slot (110); and
      iii) a first cutter (140), extending away from a longitudinal axis (X-X) of the surgical fastener combination (60), connected to an outer side (114) of the cylindrical shell (104); the first cutter (140) comprising:
         a first anterior edge (150) adapted to cut tissue in a first direction;
         a first face (152) and a second face (154) adapted to disrupt adipose, muscle, bone, joint capsule tissues, cartilage and/or bone when the first cutter (140) is rotated relative to the longitudinal axis (X-X); and
         a dull first posterior end (144);
   b) a second component (200) comprising:
      i) a shaft (210) comprising an anterior end (212) and a surgeon facing end (220), wherein the anterior end (212) is configured to ride in the hollow (108) and engage an inner wall (116) of the cylindrical shell (104) proximate the first component's anterior tip (102); and
      ii) a second cutter (240), extending away from the longitudinal axis (X-X) of the surgical fastener combination (60), connected to an outward side (214) of the shaft (210) and configured to fit within the catch (112); the second cutter (240) comprising:
         a second anterior edge (250) adapted to cut tissue in the first direction;
         a third face (252) and a fourth face (254) adapted to disrupt adipose, muscle, bone, joint capsule tissues, cartilage and/or bone when the second cutter (240) is rotated relative to the longitudinal axis (X-X); and
         a dull second posterior end (244); and
   c) a head (270) connected to the surgeon facing end of the second component (220) and adapted to receive an apparatus distinct from the surgical fastener combination (60).

2. The surgical fastener combination (60) of claim 1, wherein:
   a) an inward side (142) of the first cutter (140) attached to the outer side (114) of the cylindrical shell (104) is parallel to the longitudinal axis (X-X) and a first attachment angle (146) of the dull first posterior end (144) of the first cutter (140) is from about 30 degrees to about 155 degrees relative to the outer side (114) of the cylindrical shell (104); and
   b) an inward side (242) of the second cutter (240) attached to the outward side (214) of the shaft (210) is parallel to the longitudinal axis (X-X) and a second attachment angle (246) of the dull second posterior end (244) of the second cutter (240) is from about 30 degrees to about 155 degrees relative to outward side (214) of the shaft (210).

3. The surgical fastener combination (60) of claim 2, wherein:
   a) relative to the longitudinal axis (X-X), the first anterior edge (150) is sloped at an angle of about 30 degrees to about 155 degrees; and
   b) relative to the longitudinal axis (X-X), the second anterior edge (250) is sloped at an angle of about 30 degrees to about 155 degrees.

4. The surgical fastener combination (60) of claim 3, wherein the head (270) is a polyaxial head.

5. The surgical fastener combination (60) of claim 4, wherein the shaft (210) comprises an inner channel (222) extending from the anterior end (212) through the surgeon facing end (220) of the shaft.

\* \* \* \* \*